United States Patent [19]

Hunter

[11] Patent Number: 5,137,447
[45] Date of Patent: Aug. 11, 1992

[54] ORAL HYGIENE

[76] Inventor: Frank Hunter, P.O. Box 41, Terrigal, N.S.W. 2260, Australia

[21] Appl. No.: 671,899
[22] PCT Filed: Sep. 18, 1989
[86] PCT No.: PCT/AU89/00402
  § 371 Date: Mar. 15, 1991
  § 102(e) Date: Mar. 15, 1991
[87] PCT Pub. No.: WO90/03162
  PCT Pub. Date: Apr. 5, 1990

[30] Foreign Application Priority Data
  Sep. 23, 1988 [AU] Australia .................... PJ0578
  May 5, 1989 [AU] Australia .................... PJ4057

[51] Int. Cl.⁵ .................... A61C 19/04
[52] U.S. Cl. .................... 433/72; 33/513
[58] Field of Search .......... 433/72, 75; 128/776, 128/777; 33/511, 512, 513, 514, 556, 559

[56] References Cited

U.S. PATENT DOCUMENTS

| | | | |
|---|---|---|---|
| 910,706 | 1/1909 | Montan | 33/556 |
| 1,167,592 | 1/1916 | Neumann et al. | 33/556 |
| 3,058,225 | 10/1962 | Ward | 33/513 |
| 4,203,223 | 5/1980 | Lautenschlager et al. | 433/75 |
| 4,779,349 | 10/1988 | Odensten et al. | 33/512 |
| 4,791,940 | 12/1988 | Hirschfeld et al. | 433/72 |
| 5,000,683 | 3/1991 | Brock | 433/72 |

Primary Examiner—John J. Wilson
Attorney, Agent, or Firm—Christie, Parker & Hale

[57] ABSTRACT

An oral hygiene system includes a probe for use as a clinical measuring instrument or gauge. The probe is adapted for assessing the degree of inflamation of various animal tissues. One embodiment of the probe is useful for examination of periodontal tissues, particularly the determination of pocket depths and the degree of gingivitis. The probe has a needle member affixed orthogonally to one end of its head, and the other end of the head mounts in a handle. Between the two ends of the head there are thin resilient members adapted for transmitting an appropriate force to the tip of the needle during measurement of the depth of the pocket. Another needle member has upper and lower ends. At the lower end, there is a hemispherical tip having an angular bevel facing toward the upper end of the needle so as to form an equatorial rim about the tip. There are calibration marks extending from the tip of the needle.

17 Claims, 10 Drawing Sheets

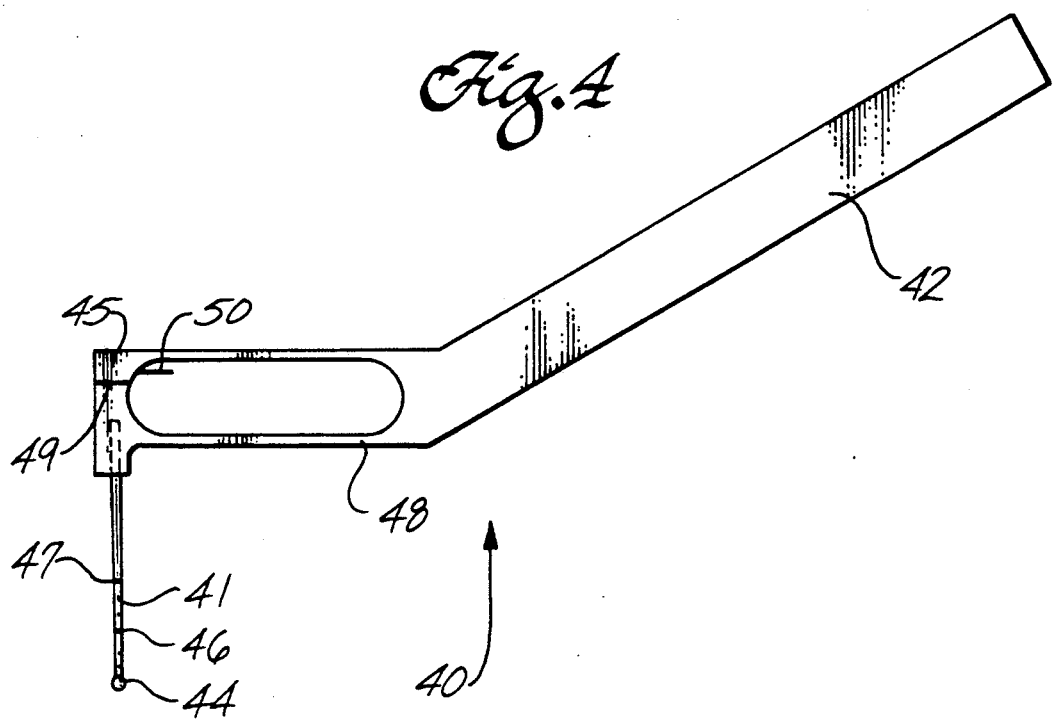
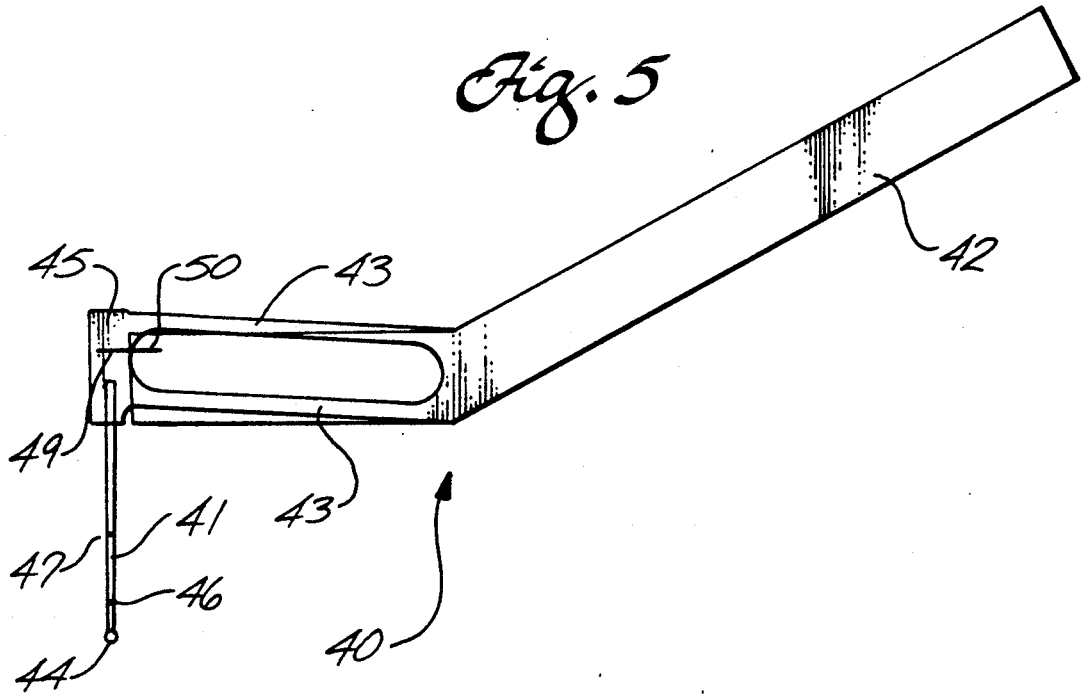

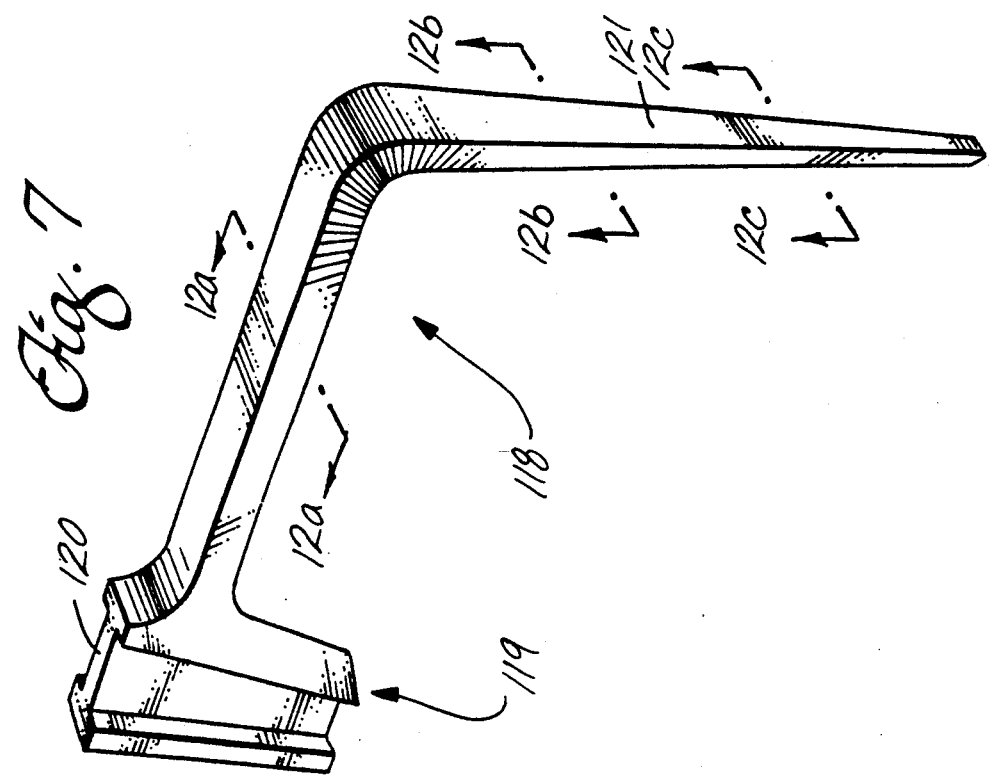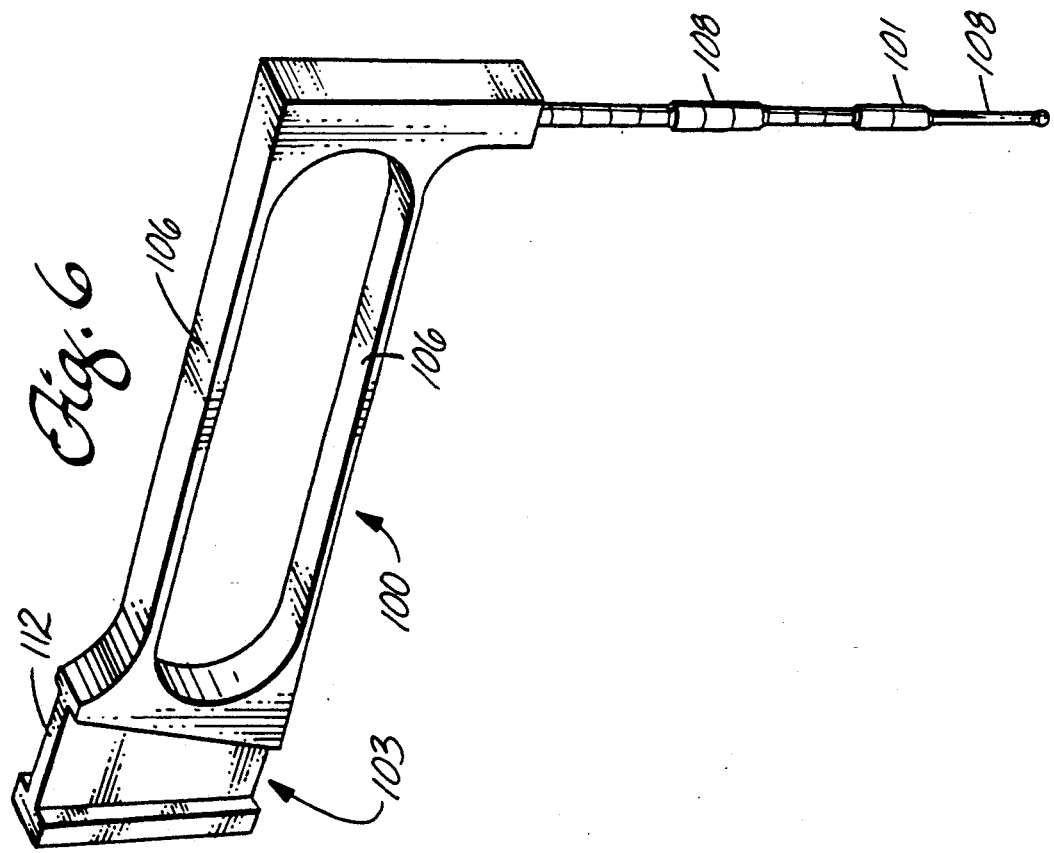

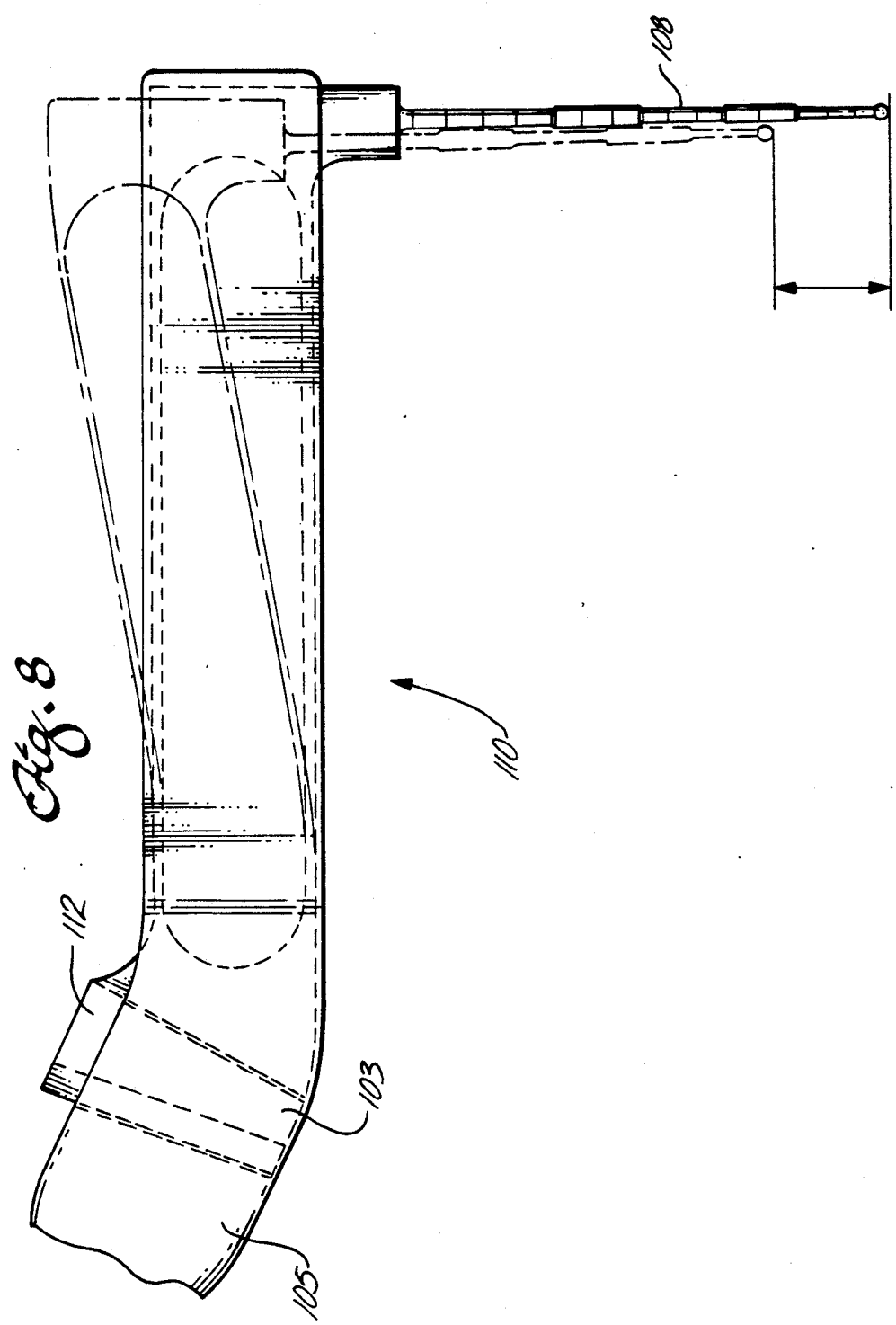

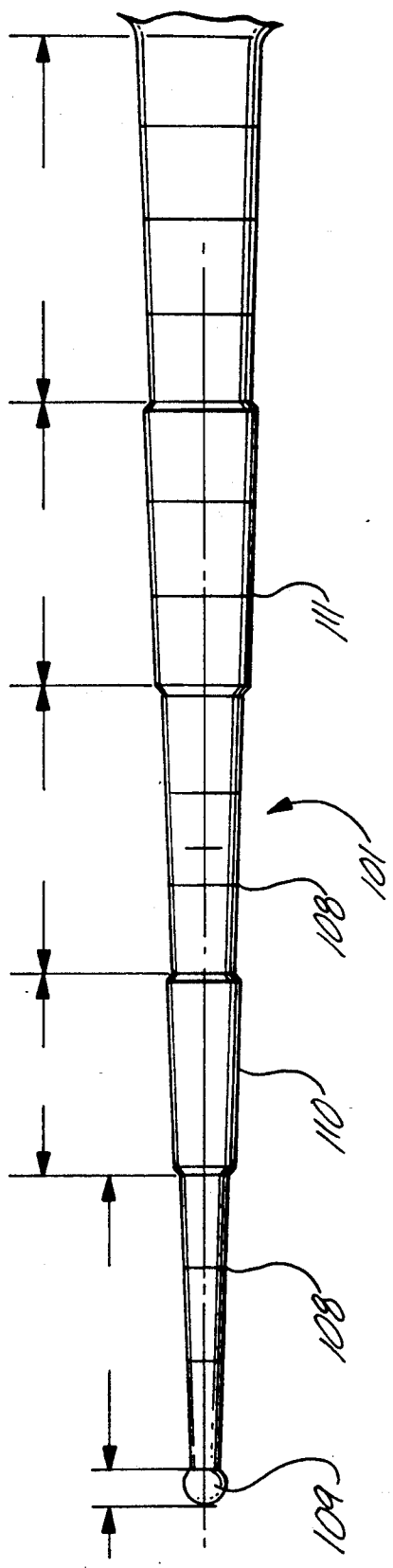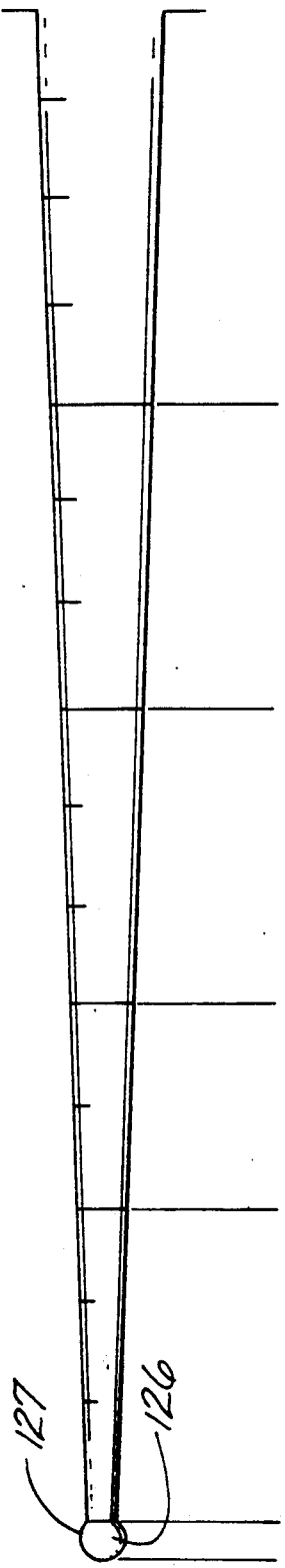

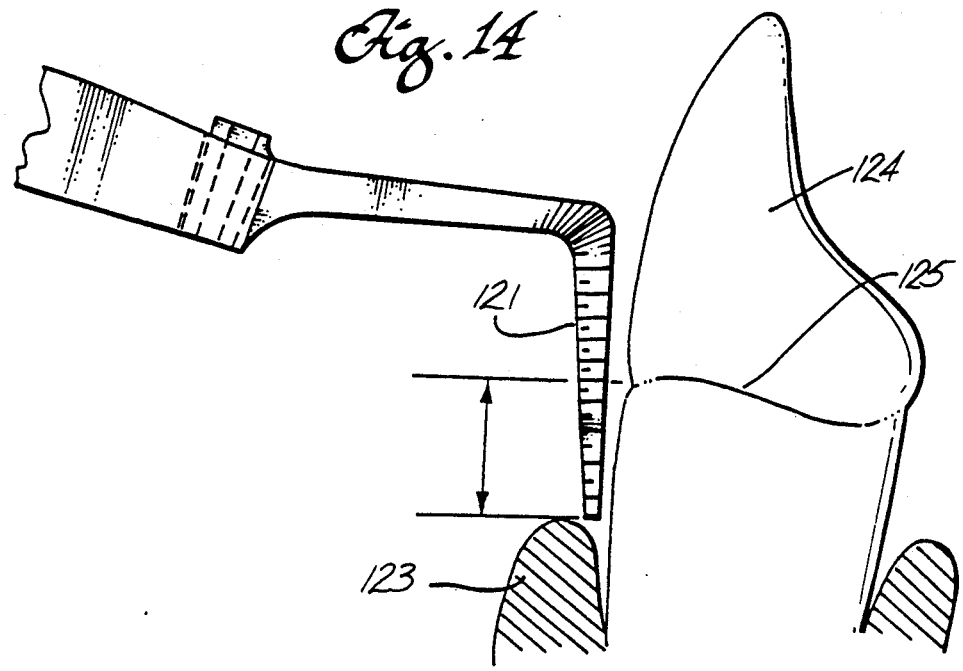
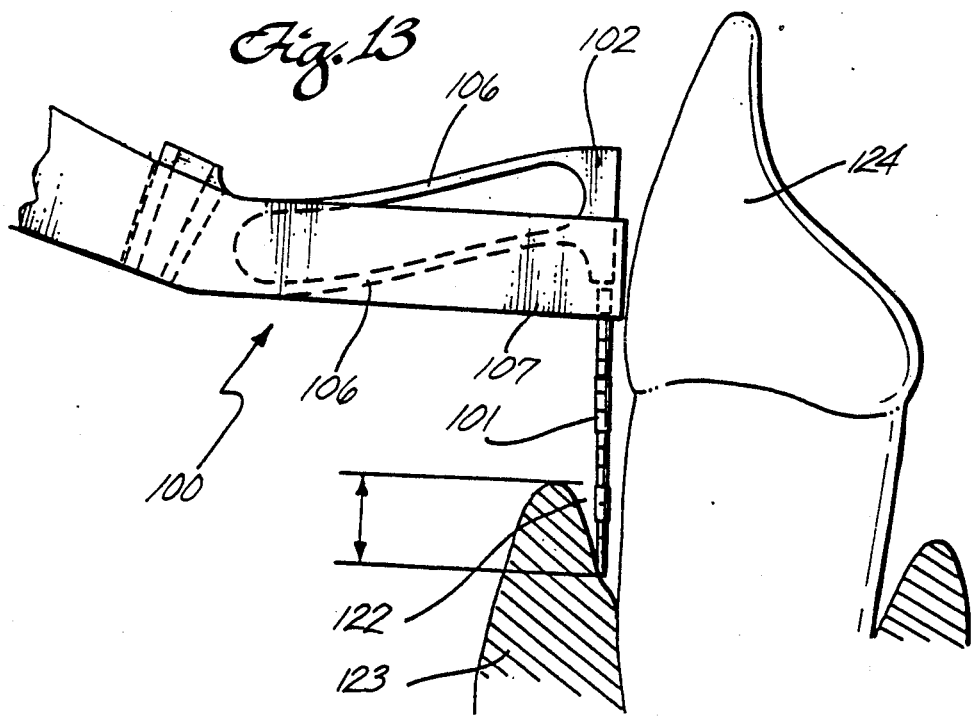

ORAL HYGIENE

TECHNICAL FIELD

This invention relates generally to improvements in oral hygiene and more specifically to a plaque disclosing composition, a toothbrushing apparatus and an instrument that is necessary in the accurate measurement of tissue status and other clinical features such as the degree of inflammation of the various tissues in animals, particularly humans and more particularly periodontal tissues, tooth mobility and basic orthodontic criteria all of which are effective when used singularly or in combination in maintaining the soft and hard tissues of the oral cavity in a healthy state.

BACKGROUND ART

It is well recognised that dental plaque is a major causative agent of caries and periodontal disease. Broadly, plaque consists of an adhesive mass of bacteria, mucins, food and other organic matter which if present for long enough on the teeth, calcifies to form calculus. Consequently, it is appreciated that the effective and complete removal of plaque is essential to the maintenance of good oral hygiene.

Unfortunately, the achievement of the goal of the removal of substantially all plaque from the oral tissues on a regular basis is not achievable by the vast majority of people, even when the individual recognises the need for plaque removal. It is therefore not unexpected that the WHO have stated that dental disease is the most common of all diseases affecting man throughout the world today.

The removal of plaque from the oral tissues at an early stage of its development may be achieved by brushing. However, if calcification occurs, then the resultant calculus may only be removed by vigorous mechanical action, usually performed by a dentist. It is therefore important to ensure plaque removal before calcification occurs.

One difficulty in ensuring that plaque is removed at an early stage is that an individual cannot readily either visually or otherwise determine if all plaque has been removed. To overcome this difficulty, the use of plaque disclosing compositions have been previously suggested. Such compositions usually consist of a dye that only stains the plaque thereby allowing its visualisation in contrast to other parts of the oral cavity.

In the prior art, these disclosing compositions have been presented in a variety of forms including rinses, lozenges, wafers and chewable tablets. It is to be noted that all of these compositions are used either before or more usually, after brushing. When used after brushing it would be expected that the composition would reveal plaque to be removed by rebrushing.

Whilst this approach has potential for the effective control of plaque, in fact the individual rarely continues the use of such disclosing composition as it requires an additional step over the normal routine of merely brushing the teeth with a dentifrice.

It is this extra step, a complicated procedure of intentional application that compromises convenience to the point where it is often abandoned or rarely maintained as a routine procedure by most people.

In Australian Patent Application 46357/79, it is taught that a disclosing agent may be included in a suitable dentifrice paste. Disclosing compositions containing mixtures of dye that result in the plaque being disclosed as a green colour are described. Such a composition would appear to meet the need for a plaque disclosing composition that is capable of being included in the normal toothbrushing routine.

It has, however, been recognized that it is important to be able to distinguish between recently formed plaque and "old" plaque. The reason for this is that "old" plaque has been found to be a causative agent of periodontal disease.

In U.S. Pat. No. 3,723,613, there is disclosed compositions that are capable of diferentially staining "new" and "old" plaque. The compositions are mixtures of dyes such as FDC Red No. 3 and FDC Green No. 3 incorporated into various formulations. In column 3, lines 29-35, it is taught that the dyes in addition to being in the form of a paint may be formulated as a chewable tablet, wafer, powders, lozenges, aerosol and liquid concentrate.

There is no teaching to suggest that such compositions could be incorporated to advantage in a dentifrice.

However, for the benefit of effective plaque disclosure to be fully translated into improved oral hygiene, the removal of this so disclosed plaque must be effective.

In the past, a variety of toothbrushing practices have been taught to be effective in removing plaque. Of necessity, such practices are at best a compromise to take account of the lack of mechanical ability of the individual, the need to effectively clean all surfaces of the teeth whilst at the same time massaging the gums without causing recession. At the same time, variations in an individual's dentition, such as the presence of prosthetic bridges, orthodontic appliances and crossed, crowded or tilted teeth means that a variety of brushing practices may be required to effectively clean all of an individual's teeth.

To meet these difficulties, a number of toothbrush head designs have been proposed and taught to be more effective in the removal of plaque.

Additionally, to overcome the lack of an individual's mechanical ability, electrically driven toothbrushes have been proposed. These are generally claimed to be more effective at plaque removal than the use of manual brushes.

Periodontal probes have been recognized in the prior art. Thus, in U.S. Pat. No. 3,058,225 (Ward) there is disclosed an instrument for automatically obtaining a measurement of attachment levels by means of a probe with a fixed sheath which engages the crown of a tooth when a measurement is made. A slidable needle is moved through the sheath into the periodontal pocket. The distance between the tip of the needle and the end of the sheath, being substantially the periodontal attachment level, is determined electrically by varying the resistance of a resistor in engagement with the needle.

U.S. Pat. No. 3,943,914 (Grenfell et al.) there is disclosed a periodontal probe wherein pocket depth is measured using a stationary needle and a sheath which slides on the needle to the edge of the gingival margin of the pocket when the needle's tip engages the bottom of the pocket. The distance between the end of the sheath and the tip of the needle is converted into an electrical signal to provide an indication of the depth of the periodontal pocket. The electrical signal is recorded on a chart recorder or other means to provide a visual, permanent record.

In U.S. Pat. No. 4,677,756 (Simon et al.) a probe is disclosed comprising a pair of probe elements moveable relative to one another to vary the spacing between sensing areas of each probe, means for producing a signal representing the spacing of said sensing areas, means for monitoring the rate of charge of said signal, and means for recording and/or displaying a value representative of said signal upon the rate of charge of said signal reaching a predetermined value.

It is to be noted that none of these patents in any way control the force at which probing is conducted.

In U.S. Pat. No. 4,340,069 (Yeaple) there is disclosed a probe in which the probing force used to determine pocket depth is predetermined. The probe comprises a magnetizable member mounted within the probe body. A movable lever is also mounted within the body and has a probe tip insertable into a periodontal pocket. The lever has a portion thereof formed from a magnetic material and is further movable between an "engaged" position in which the lever portion is attracted to and engages the member, and a "disengaged" position in which the lever portion is disengaged from the magnetizable member. The probe also comprises means for magnetizing the magnetizable member for releasably holding the lever in its "engaged" position with a preset magnetic force. In this position, the probe is adapted to be inserted into a periodontal pocket and a manual probing force applied thereto when the end of the probe engages the floor of the pocket. When the probing force is increased to the predetermined probing force value, it overcomes the preset magnetic force generated by the magnetizing means causing the lever portion to be moved to its "disengaged" position. The depth of the pocket can then be observed and read on a depth measuring scale on the probe tip for the predetermined probing force.

In PCT/US88/02749 (W089/01314), there is disclosed a periodontal probe system for measurment, storage, and display of periodontal pocket depth, gingival level, and periodontal attachment level of the teeth. The periodontal probe instrument includes an elongate tip with a measurement arrangement that simultaneously measures periodontal pocket depth, gingival level, and periodontal attachment level at each of a plurality of probe sites around a tooth. A pressure sensor in the probe provides a pressure signal indicative of the pressure acting on the tip of the probe. A periodontal measurement is made by inserting the tip of the probe into a gum pocket and gradually increasing the pressure on the probe tip after insertion. At a predetermined pressure leval, the signal processing apparatus samples the depth signals and converts them into measurement signals corresponding to pocket depth and attachment level.

Whilst it would appear that this probe system offers advantages over the prior art, on pages 3 and 4 it is taught that measurement of pocket depth and attachment level are made with reference to the top of the crown of a tooth. This is illustrated in FIG. 2. The difficulty in using the top of the crown as a reference point is that because the crown wears with time, it is not a consistent reference point. In addition, phenomena such as tilting teeth, cusp fracture, restorative procedures and coronal fracture will affect the consistency of the crown as a reference point.

Furthermore, the crowning of a tooth will significantly alter the height of the reference point.

It is therefore evident that this probe system is not adapted to provide a reliable reference point or history of pocket depth development and level of attachments relative to an established permanent reference point.

Because the probe system uses transmission of light to activate light sensitive devices as a measure of pocket depth, any variation in transparency of gum tissue from patient to patient will cause a variation in depth measured. For example, there may be a substantial difference in transparency between the gums of a 5 year old child and the gums of a 65 year old adult. In addition, there are different amounts of melanin and/or keratin in various ethnic, racial and behavioural populations. Thus discrepencies are evident in the density of tissue amongst these groups and even at various sites in the same mouth.

From the foregoing discussion it is evident that all of the prior art probes mentioned are elaborate and sophisticated devices which compromise obvious requirements. Thus, these probes in use would tend to interfere with a dentists need to carefully assess disease pattern and pathology in an effective, practical and economical way.

SUMMARY OF THE INVENTION

Accordingly, the present invention in a first aspect consists in a plaque disclosing composition for use in the control of dental plaque, comprising a dentrifice base, an effective amount of FDC Red No. 3 and an effective amount of at least one dye selected from the group consisting of FDC Blue No. 1, FDC Green No. 3, Hercules Green Shade 3 and sodium fluorescein.

The inventive composition has dual advantages, the first of which is that it can be used as a substitute for a standard dentrifice either on all toothbrushing occasions or on a routine basis Thus the only additional step that needs to be taken over regular toothbrushing is the brushing of those portions of the teeth on which plaque has been disclosed, that is, the continuance of brushing until the dye is removed. This eliminates the need for an extra step.

The second advantage lies in the ability to be able to distinguish "new" from "old" plaque This allows a user to ensure that "old" plaque is expeditiously removed to prevent the onset of periodontal disease.

The compositions of the invention may be formed by the addition of the selected dye to a wide variety of dentrifice bases. Such dentrifice bases will include conventional abrasives such as colloidal silica, calcium carbonate, calcium pyrophosphate, aluminium hydroxide and the like.

Preferably, a fluoride containing species such as sodium or calcium monofluorophosphate or a stannous fluoride is included in the dentrifice base.

Other art recognised additives such as thickening and suspending agents, surfactants and flavourants may be included in the dentrifice base as required.

The amount of the selected dye to be included in the dentrifice will be sufficient so as to adequately disclose plaque in the oral cavity.

From the description of the aforementioned plaque disclosing composition, it will be evident that the regular use of such a composition provides a means by which the presence of plaque may be visualised.

Indeed, the dye combination may trace the organisational structuring of plaque through its various stages of maturity and thereby demonstrate its pathogenicity towards various tissues of the mouth to the user at each brushing episode. Only with this facility may the need for effective brushing be reinforced each time the dentrifice is used.

In order to give effect to the plaque disclosure aspect of the invention, the present inventor has recognised that there exists a need for a toothbrush that is capable of effective plaque removal when used by an average individual with or without variable dentition.

Accordingly, in a second aspect, the present invention consists in a toothbrush comprising a head and handle, said head being provided with an array of upstanding bristles formed at an upper end thereof into an inverted "V" shape.

This has been shown to be particularly effective in periodontal, interproximal and bifurcation hygiene.

In another form of this aspect, the array of bristles is formed into two adjacent square or rectangular pyramidal shapes that extend along the length of the head.

This has been shown to perform excellent universal plaque removal.

Where the array of bristles is formed into the shape of an inverted "V", it has been shown to be of importance in areas of specific difficulties.

One advantage of the inventive toothbrushes are that there is a "self-seating" effect when the head is applied to the buccal or lingual surfaces of a tooth. The apex of a head will penetrate into the depth of the interproximal area.

Ideally, the slope of the head should be the same as the buccal and lingual contours of each tooth. However, as a practical matter, because of the variations in contours, the slope of the head will approximate these contours. In this embodiment the bristle pressure will therefore be equally distributed over the surface of each tooth.

Thus, the precise motion and force necessary to perform plaque removal is automatically directed to the required site. Approximately 85% of dental disease commences interproximally and the topographic contour of these pyramidal surfaces are so designed as to deliver 85% of their cleaning action forces to this site.

Further advantages of the inventive toothbrushes are that:

(a) as the brush is moved from one tooth to the neighboring one, and so around the mouth, each interproximal area is serviced by both peaks separately. Thus, there is a double cleaning of each otherwise vulnerable interproximal area;

(b) when viewed from end-on, the peak is seen to coincide with the contact points of teeth and so most cleaning is directed to where it is most needed; and (c) lateral pressure brings about an automatic or subconscious self-seating and a sliding into the interproximal area by neighboring bristles and so population density of bristles is increased thereby improving cleaning efficiency.

As previously mentioned, various difficulties are encountered, such as crowding, crossing and tilting of teeth, prosthetic and orthodontic appliances. The third form of the inventive toothbrush is particularly useful in respect of such teeth. The reason for this is that the "V" stands in the interproximal space and by appropriate movement, may be caused to sweep across this space.

Finally, this head has been shown to perform adequate cleaning of periodontal pockets. The bristles are so trimmed as to permit convenient penetration into the periodontal pockets. The motion is such as to provide adequate removal of plaque from this otherwise inpenetrable region. The present inventor has shown that use of this attachment effectively reduces the pocket depth to a point where it is no longer of pathologic consequence or concern. Moreover, advanced periodontal disease may be eliminated or eventually reversed by application of this procedure.

Although the aforementioned toothbrushes may be used to advantage when operated manually, the present inventor has established through extensive research that the control of motion of these toothbrushes over the surfaces of the teeth is important to maximise the effectiveness of plaque removal whilst avoiding the promotion of gum recession.

Ideally, the brushhead moves over the surface of a tooth in an arc equivalent to the coronal height of a tooth. The travel of the bristles thus terminates in the gingival crevice and so does not disturb the periodontal fibres or their attachment of the gum to the tooth.

Preferably, the circumference of the arc made by the bristles will approximate the contour of the interproximal surface of the teeth and thereby achieve continued sweeping of that surface by the bristles as they move around this arc.

However, it will be apparent that the achievement of this movement manually would require considerable dexterity and has been generally shown to be beyond achievement.

In recognition of this, the present inventor has realised that by appropriately modifying the electrically driven toothbrush described in Australian patent 550522 and corresponding foreign equivalents, the toothbrushes of the invention may be attached thereto and caused to oscillate in the arcuate manner described.

To achieve this arcuate motion, the aforementioned electrically driven toothbrush is provided with an eccentrically placed pin rotating on a circular shaft and riding within a groove provided in the head of the toothbrush.

It is preferred that the circular shaft and pin be formed from a material so as to be durable relative to the longevity of the bristles and the groove. Most preferably, the groove will become inoperably worn at the time the bristles are no longer acceptable for use.

The present inventor has found that where the inventive toothbrushes are used with the aforementioned electrically driven toothbrush, plaque removal is approximately four times better than when a conventional electric toothbrush is used.

Whilst the oscillating twin and single-peaked heads have been shown to be superior in the universal removal of plaque especially in interproximal, periodontal, prosthetic and orthodontic situations, the inventor recognizes the benefit in either routine or occasional topical application of certain substances. This may best be achieved by a rotating brush with a particular array of radially disposed bristles in a spiral arrangement. The present invention has been designed so as to permit the alternate attachment of this facility to the device by special design and selection of gearbox, speed, torque and direction change. In this regard it is to be noted that the present arrangement permits engagement of the brush on the one rotating drive in contrast with the arrangement described in Australian Patent 550522 which required separate drives.

The use of the rotating brush is not claimed to be essential in all cases but rather to be an advantage in certain situations. It is thus offered as a selectable or alternative addition to the basic device without alteration of design.

It will, however, be realized by those skilled in the art, that other mechanical toothbrushing apparatus may be used in place of the aforementioned prior art device.

The aspects of the invention that have been described have related to improvements in the disclosure and the removal of plaque, both of which will be performed by the individual.

However, the diagnosis of periodontal disease and the determination of the presence of plaque and calculus, particularly in the cervical margins, gingival crevice, periodontal attachment and deeper advancing pockets, will be performed by the dentist. Currently, the World Health Organisation (WHO) recommends the use of a probe which is inserted into the periodontal pocket and the depth of penetration measured. The extent of penetration will be proportional to the degree of periodontal disease present.

To measure depth of penetration, the probe is provided with at least four marks indicating 3.5, 5.5, 8.5 and 11.5 mm depths. A range of other depths may be indicated. The total length of the probe should be 15 mm.

As the periodontal pocket consists of relatively soft tissue, the amount of force exerted on the probe should ideally be standardised. The WHO has recommended the use of 20-25 grams of force. A lower force may be indicated where the tissues are highly inflamed. However, the means by which this force is measured is highly subjective and is therefore quite variable.

The present inventor has recognised the desirability of being able to accurately exert a reproducible force of about 20-25 grams in the use of such a probe, or such other standard forces that may be chosen.

Accordingly, the present invention provides in a third aspect, a gauge in the form of a dental probe for use in measuring the depth of a periodontal pocket the level of gingival height and the degree of gingivitis comprising a needle member, an upper end of which is mounted in a head, and a handle attached to the head by a resiliently deformable member, said head and said handle each having a mark thereon which when no force is exerted on the needle member are out of alignment but when a selected force is applied, will be aligned.

As mentioned above, preferably the selected force will be from about 20-25 grams. Moreover, the needle member will preferably be provided with at least four marks at 3.5, 5.5, 8.5 and 11.5 mm distances from the end thereof to indicate corresponding periodontal pocket depth.

Advantageously, the tip of the needle member should be blunt and preferably hemispherical, 0.5 mm in diameter, to assist in the detection of calculus and plaque in the cervical margins and related deeper regions. The tip has an equatorial rim.

The resiliently deformable member will preferably comprise two substantially parallel elongate members.

As in use the probe may be disposed of after each individual's examination, which will generally comprise the probing of up to 32 teeth, each tooth being probed at 6 points, the robustness of the resiliently deformable member will be such as to provide a reproducible force over at least 200 readings.

The inventive gauge, including the needle member, may be formed from a variety of synthetic plastics materials such as acrylic, polycarbonate and SAN. Alternatively, the probe may be formed wholly of metal such as aluminium or the needle member may be of metal whilst the remainder of the probe is plastic.

In addition to the measurement of periodontal pocket depth, the present inventor has recognised that there exists a need to measure the extent of gum recession in conjunction with pocket depth. The reason for this is that a receded gum will reduce the apparent pocket depth.

Accordingly, in a preferred embodiment, the handle of the probe is adapted to mount a second probe at its other end or a means for measuring the extent of gum recession. The gum recession measurement means may conveniently be calibrated in mm divisions. A further use being to record plaque and other indices; orthodontic features such as cross-bite, overjet and over bite, etc., and indeed all clinical examination data such as tooth mobility, occlusion, and other clinical features.

In addition, a still further advantageous probe may be obtained by providing a handle that has at one end a means for receiving the head and at the other end a connection means that allows a like nd of another such handle to be joined thereto. Alternatively, a handle having a connection means at one end and at the other end a means for receiving the gauge for measuring gum recession, or other features may be joined thereto.

Advantageously, the needle member is disposable or more preferably those portions of the probe coming into contact with the tissues of the oral cavity are able to be discarded thereby eliminating the possibility of transmission of microorganisms to a subsequent patient. These portions will generally comprise the head of the probe. Note that it is possible to produce a probe that is capable of steam sterilization, that is, one not having a disposable head. However, because of the difficulty of cleaning, the WHO have recommended disposable heads.

BRIEF DESCRIPTION OF THE DRAWINGS

In order to more fully understand the nature of the invention, there follows a description of a number of examples of the invention in which:

FIG. 4 shows in side view a first example of a gauge in the form of a dental probe of the invention;

FIG. 5 shows in a side view, the probe of FIG. 4 when a force of 25 grams is exerted;

FIG. 6 is a perspective view of the head of a second example of a probe of the invention for use in periodontal pocket depth evaluation;

FIG. 7 is a perspective view of the head of a gauge of the invention for use in the measurement of gum recession;

FIG. 8 is a partial side elevational view of the head of the probe of FIG. 1 mounted in a handle of the invention;

FIG. 9A is an exploded side elevational view of the needle member of FIGS. 6 and 8;

FIG. 9B is an exploded side elevational view of an alternative needle member;

FIG. 14 is a schematic view of the gauge of FIG. 7 in use; and

MODE(S) FOR CARRYING OUT THE INVENTION

Figure 1A:
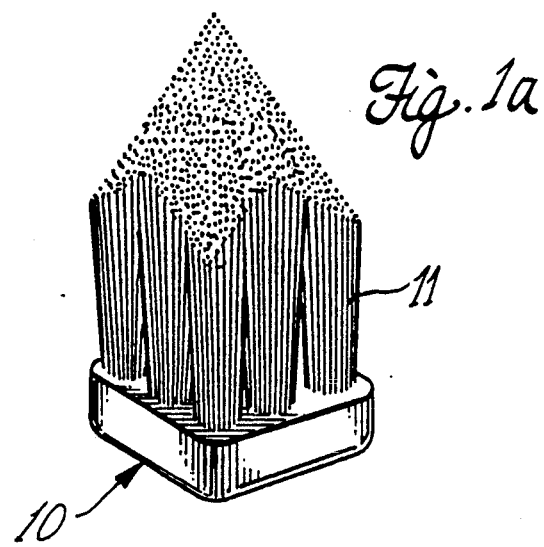
FIG. 1 shows a first example of a toothbrush of the invention in
(a) perspective view,
(b) plan view,
(c) inverted plan view, and
(d) side view.
Figure 1B:
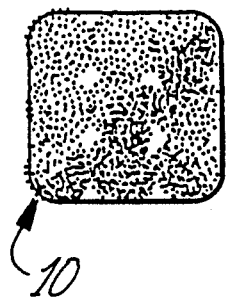
Figure 1C:
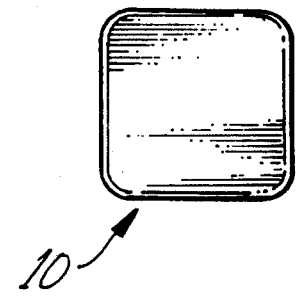
Figure 1D:
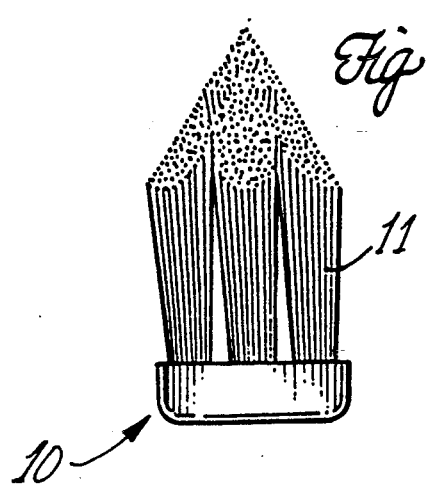
Figure 2A:
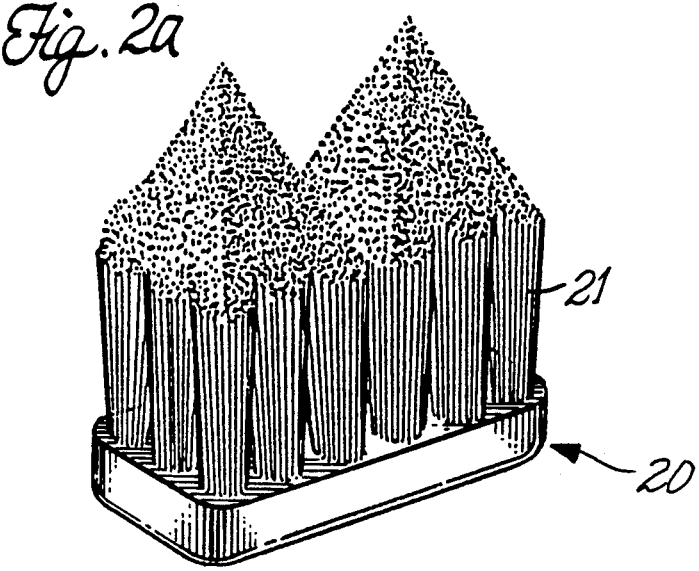
FIG. 2 shows a second example of a toothbrush of the invention in
(a) perspective view,
(b) plan view,
(c) inverted plan view,
(d) side view, and
(e) end view.
Figure 2B:
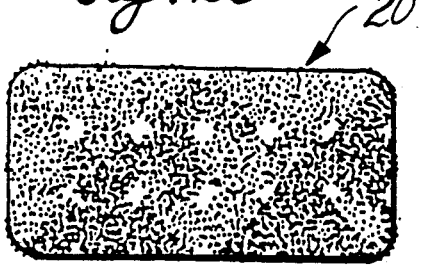
Figure 2C:
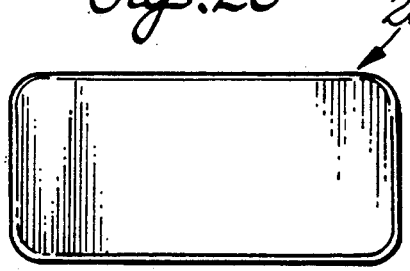
Figure 2D:
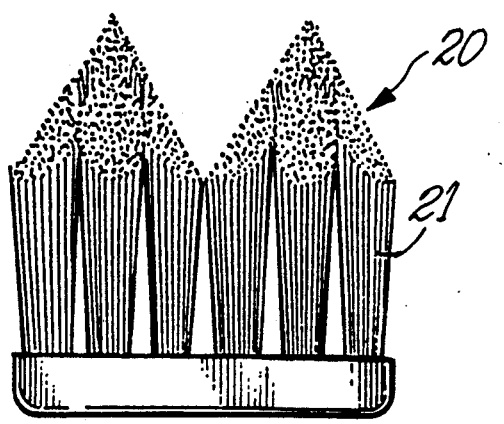
Figure 2E:
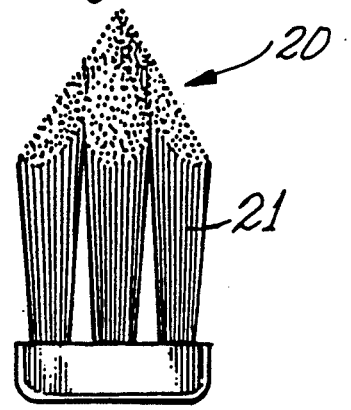
Figure 3A:
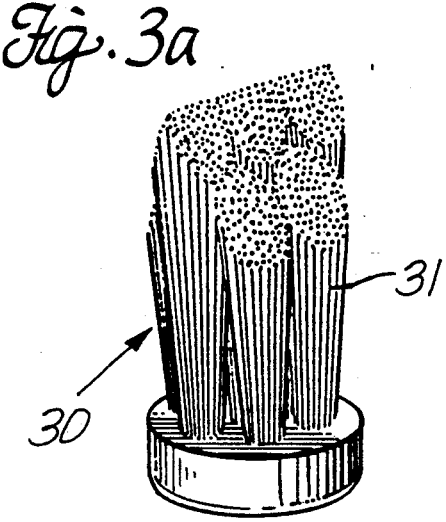
FIG. 3 shows a third example of a toothbrush of the invention in
(a) perspective view,
(b) plan view,
(c) inverted plan view,
(d) side view, and
(e) end view.
Figure 3B:
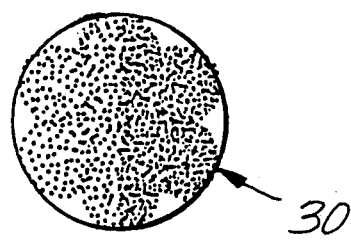
Figure 3C:
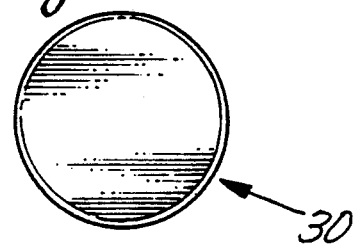
Figure 3D:
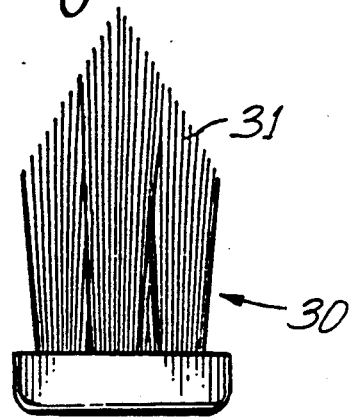
Figure 3E:
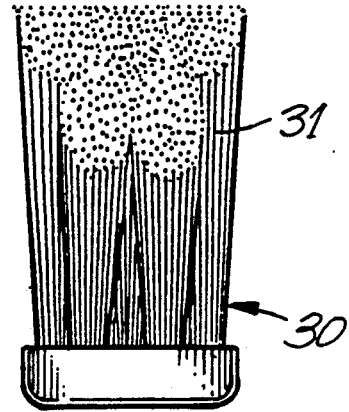

In FIG. 1(a)–(d) there is shown the head of a toothbrush 10 in which the bristles 11 have been shaped to provide a generally pyramidal shape. The bristles are 612 nylon which may have a width of from 0.008 to 0.014 inches.

Similarly, there is shown in FIG. 2(a)–(e) the head of a toothbrush 20 in which the bristles 21 have been shaped to provide two side by side generally pyramidal shapes.

In FIG. 3(a)–(e) there is shown the head of a toothbrush 30 in which the bristles 31 have been shaped into a V.

As shown in FIGS. 4 and 5, the probe 40 comprises a needle member 41, a handle 42 and a resiliently deformable member 43. The needle 41 has a ball 44 at the end thereof having a diameter of 0.5 mm. Immediately behind the ball, the needle reduces to the vicinity of 0.3–0.4 mm in diameter tapering upwardly to 1 mm at the end in the head 45. The length of the needle is 15 mm from the center of the ball to where it enters the head.

At reference numerals 46 and 47, there are marks on the needle 41 representing depths of 3.5 mm and 5.5 mm respectively, according to CPITN, superimposed upon the mm calibration marks.

The remainder of the probe is formed from acrylic.

The resiliently deformable member 43 comprises two elongate members which are visible in FIG. 5. In FIG. 4, plates 48 disposed either side of the members 43, to prevent sideways movement thereof, are shown.

On head 45, there is a mark 49 which when aligned with the mark 50 disposed on a plate 48, indicates that a particular predetermined force of is being exerted on the needle.

Figure 11:
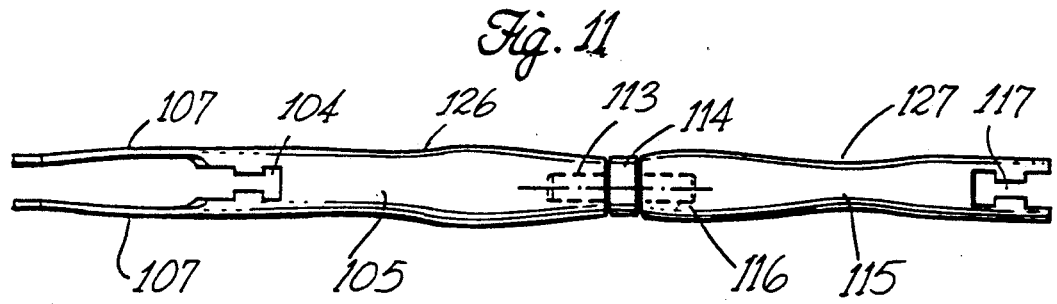
FIG. 11 is a plan view of the handle of FIG. 10.

In FIG. 6, there is shown as reference numeral 100, the head of a probe of the invention for use in the evaluation of periodontal pocket depth. The head 100 has a needle member 101 affixed orthogonally to an end 102 distal a shaped end 103 adapted to be mounted, as shown in FIG. 11, in a correspondingly shaped opening 104 of a handle 105.

Extending between the end 103 and the end 102 are two parallel, planar, relatively thin resilient members 106. These members are adapted to transmit an appropriate force to the tip of the needle member 101.

The head is preferably formed from a synthetic plastics material.

Handle 105 has at one end shaped opening 104 to receive the head 100. At the same end, there are two plates 107, each extending from opposing sides of the handle. These plates are spaced sufficiently apart to accommodate the width of the resilient members 106 and have a length such that an outer face of the end 102 lies proximate the ends of the plate 107. They function to protect the resilient members 106 and to bear an appropriate mark to indicate when a selected force is applied to the needle member 101.

In order to facilitate the measurement of pocket depth, the needle member 101 is calibrated along its length in mm divisions 108. This is best seen in FIG. 9A. At a lower end, there is a spherical tip 109 which is 0.5 mm in diameter. Immediately behind the tip, the needle reduces to about 0.3–0.4 mm in diameter tapering upwardly to a width of 1 m where it enters the head at end 102. The overall length of the needle is 15.5 m.

At reference numeral 110, there is a widened or otherwise marked portion of the needle, the lower edge of which is 3.5 mm from the tip 109, whilst the upper edge is 5.5 mm from tip 109.

A second portion 111 is similarly widened or marked, the lower edge being at 8.5 mm whilst the upper edge is 11.5 mm from the tip. It has been found in use that measurements to + or −0.5 mm are possible. Note that it is important these zones be visually recognizable. Features which provide this include colour, polish, finish or other visible features.

In FIG. 9B there is shown an alternative needle member which in all respects is the same as the needle member shown in FIG. 9A except that the tip 126 is not spherical. Tip 126 is hemispherical at its lower end with an angular bevel towards the body of the needle member, thus creating an equatorial rim 127. This rim 127 is advantageous in detecting the detail of subgingival anatomy, calculus adhesions, root anatomy or any other features.

The needle is preferably formed from stainless steel or other appropriate materials, whilst the divisions 108 are created by etching, machining, spark erosion or other means. By appropriate material, it is meant that the needle member must be capable of transmitting tactile sensation for the detection of calculus and general anatomy.

As is best seen in FIG. 8, when the head 100 is placed in the handle 105, by sliding end 103 into opening 104, a portion of the shaped end 103, shown as 112, will project above an upper surface of the handle. As a consequence of the taper of the shaped end 103 and the taper of the opening 104 increasing upwardly, appropriate pressure exerted downwardly at 112 will cause the head to be ejected from the handle. This facilitates the easy disposal of the head.

Figure 10:
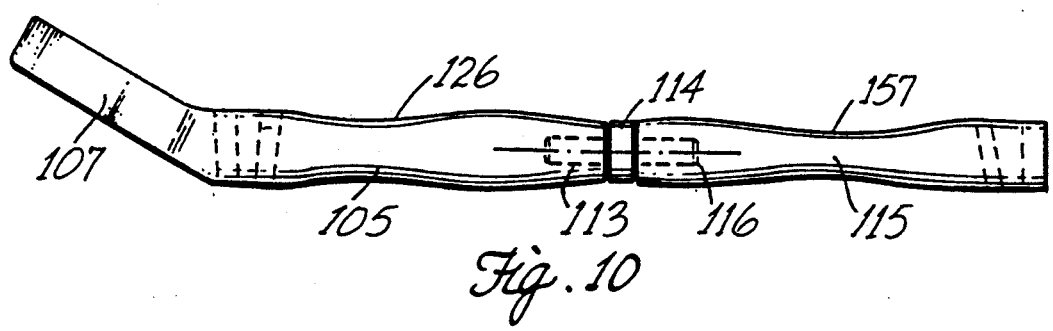
FIG. 10 is a side elevational view of a handle for use with the probe of FIG. 6 and the gauge of FIG. 7.

As is shown in FIGS. 10 and 11, the handle 105 may have an opening 113 at its other end to receive a plug 114 thus facilitating its connection to a second handle 115 having a like opening 116 to receive the plug.

In the embodiment shown in FIGS. 10 and 11, the handle 115 has a shaped opening 117 to receive a gauge for measuring gum recession. The gauge 118 is best seen in FIG. 7. In that figure, the gauge 118 is shown to have a shaped end 119 adapted to slide into the shaped opening 117 in the handle. The end 119 has a portion 120 that projects above an upper surface of the handle 115. This permits the head 118 to be ejected from the handle by exerting appropriate pressure at 120.

Figure 12C:
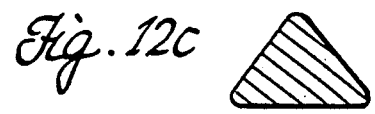
FIGS. 12(a)–12(c) are sectional views taken along lines 12a–12a, 12b–12b and 12c–12c, respectively, of FIG. 13 is a schematic view of the probe of FIG. 6 in use.
Figure 12B:
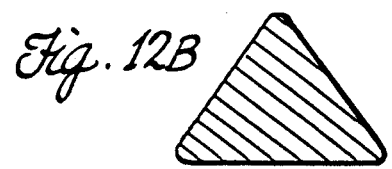
Figure 12A:
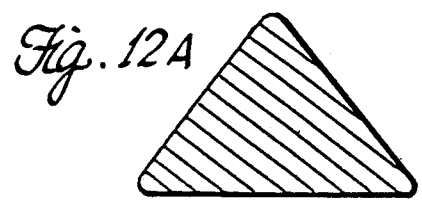

The gauge 118 has a portion extending away from end 119 and then a measurement portion 121 extending orthogonally downwardly. As shown in FIGS. 12a, b and c, this portion of the gauge is triangular in section.

As was previously stated, pocket depth measurements are to be taken when a force of 25 gms was exerted on the tip 109 of the needle member 101. A reproducible 25 gm force may be achieved by a variety of means of which one is to have a mark on end 102 which when it is aligned with the mark on plate 107 will correspond with a force of 25 gm. However, this may be so designed to operate at 20 gm or any other appropriate force.

In FIG. 8 the head is shown in two positions, solid lines representing at rest and broken lines representing force applied to the tip. The measurement shown is approximately 4 mm.

The inventive probe is shown in use in FIG. 13 to measure a periodontal pocket depth of 5.5 mm. The needle member 101 has been pushed into the pocket 122 between the gum 123 and the tooth 124 until a force of 25 gms has been achieved on the tip. At that point the resilient member 106 has been displaced upwardly until a mark (not shown) on end 102 is aligned with a mark (not shown) on plate 107. The divisions on the needle member have then been read off to give a depth of 5.5 mm.

The gum recession gauge 118 is shown in use in FIG. 14. In this instance, the lower end of the measurement portion 121 has been aligned with the gingival margin whilst the neck 125 of the tooth 124, or more specifically the cemento-enamel junction, has been aligned against the scale. A reading of 5 mm is shown. This measurement may be referred to as the "gingival recession factor".

In order to facilitate the taking of measurements, handles 105 and 115 are each provided with a raised portion 126, 127 respectively. These allow the thumb and index fingers to be placed either side of the handle, whilst the middle finger supports the handle from the underside. This represents the conventional pen grip.

In order to allow the measurement of the gingival recession factor at a particular force, the probe 101 and gauge 118 are interchangeable. Likewise, handles 105 and 115 are also interchangeable.

Figure 15C:
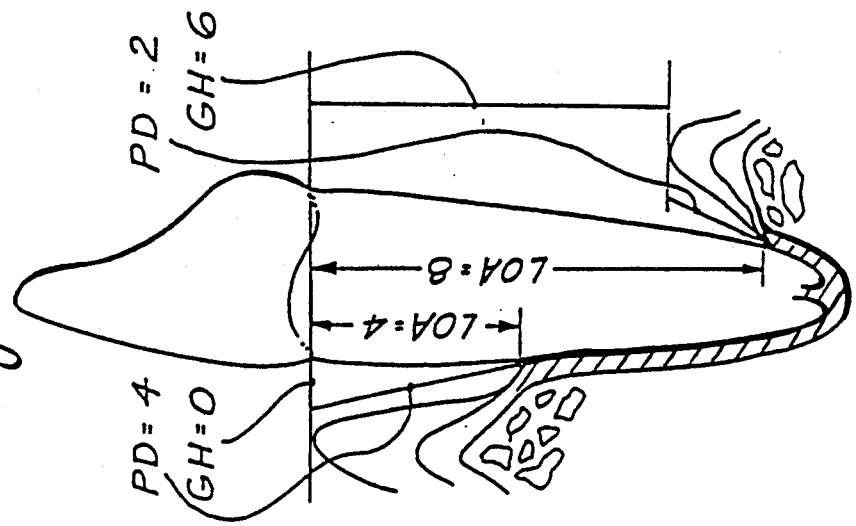
FIG. 15A, B & C are schematic views of teeth showing varying loss of attachment.
Figure 15B:
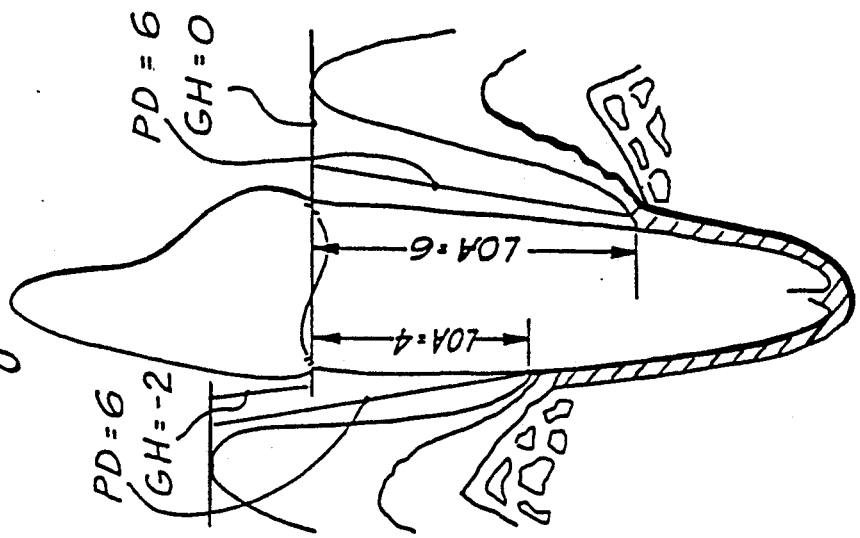
Figure 15A:
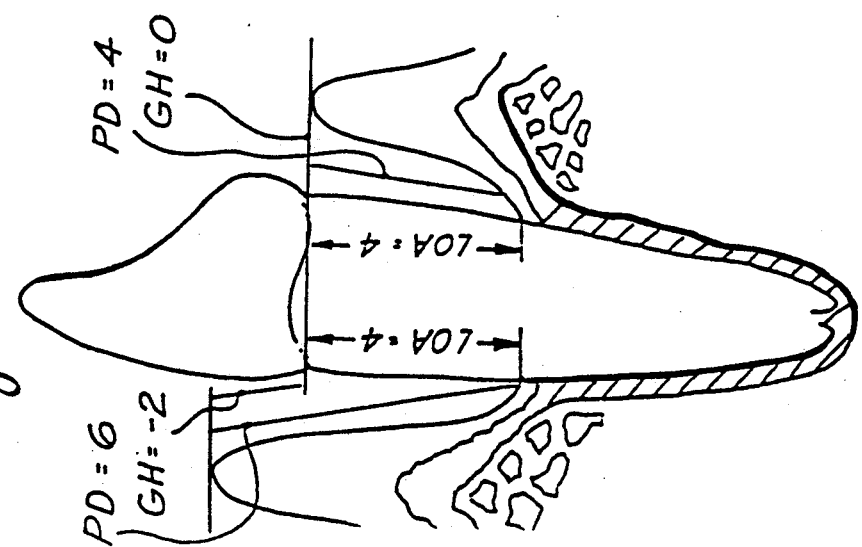

In FIGS. 15A, 15B and 15C, there are shown three teeth A, B and C exhibiting varying loss of attachment (LOA). Loss of attachment is the sum of pocket depth (PD) and gingival recession (GH). It is therefore obvious that the recording of pocket depth and gingival recession are essential elements in calculating the loss of attachment of a particular tooth. It is this loss of attachment which represents a critical value in assessing the longevity, prognosis or status of a tooth in situ.

The importance of the calculation of LOA from PD and GH measurements is illustrated in FIGS. 15A, 15B and 15C. Thus, in tooth A, 1 and 2 have identical LOA, although 1 has a 50% deeper pocket than 2. In booth B, 3 and 4 have identical PD but 4 has a 50% greater LOA than 3. In tooth C, 5 has twice the pocket depth of 6 but 6 has twice the LOA of 5.

Although the foregoing description has been directed towards a probe for use in the assessment of the periodontal region of the mouth, it will be recognised that with appropriate force calibration, a probe could be used to determine the health of a variety of tissues by measuring an "odaematous inflammatory factor". This would be achieved by measuring needle displacement at a selected force for a variety of healthy tissues and then comparing these with results obtained from suitably diseased tissue.

I claim:

1. A probe adapted for use as a clinical measuring instrument or gauge comprising a needle member, an upper end of which is mounted in a head, and a handle attached to the head by a resiliently deformable member, said head and said handle each having a mark thereon which when no force is exerted on the needle member are out of alignment but when a selected force is applied, will be aligned.

2. A probe as in claim 1 wherein it is adapted for use as a periodontal pocket probe.

3. A probe as in claim 2 wherein the resiliently deformable member is adapted to align the marks at a force of up to 25 grams.

4. A probe as in claim 3 wherein the needle member is provided with a series of marks along its length to permit depth measurement.

5. A probe as in claim 2 wherein the needle member has a spherical tip.

6. A probe as in claim 2 wherein the needle member has a tip which is hemispherical at its lower end with an angular bevel towards the body of the needle member to create an equatorial rim.

7. A probe as in claim 2 wherein the handle is adapted at an end opposing the head to mount a second probe or a means for measuring the extent of gum recession.

8. A probe as in claim 7 wherein the handle has at end opposing the head a connection means that allows a like end of another such handle to be joined thereto.

9. A probe as in claim 1, wherein the needle member is disposable.

10. A probe as in claim 9 wherein the head and needle member are disposable.

11. A probe as in claim 10 wherein the handle has a shaped opening adapted to receive the head, comprising two plates each extending from opposing sides of the handle and spaced apart to accommodate the resilient members.

12. A probe as in claim 11 wherein at least one of the plates bears a mark for alignment with a corresponding mark on the head to indicate when a selected force has been applied to the needle member.

13. A probe as in claim 12, wherein a portion of the head projects above an upper surface of the handle such that when force is exerted downwardly on this portion, the head is ejected from the handle.

14. A needle member adapted for use in a probe which functions as a clinical measuring instrument or gauge, comprising an elongate member having an upper end and a lower end, at the lower end there is a hemispherical tip facing away from the elongate member and having an angular bevel facing the upper end of the elongate member so as to form an equatorial rim about the tip, and the upper end of the elongate member includes means for mounting said needle member in said probe, the elongate member having calibration marks disposed thereon.

15. A needle member as in claim 14 wherein the elongate member tapers from the upper end to the lower end.

16. A needle member as in claim 13 wherein the calibration marks constitute mm divisions.

17. A needle member as in claim 14 wherein the calibration marks extend along a length of the elongate member starting from the lower end.

* * * * *